United States Patent
Fujiyama et al.

(10) Patent No.: US 10,336,987 B2
(45) Date of Patent: Jul. 2, 2019

(54) LIVER TISSUE CULTURING DEVICE, LIVER TISSUE CULTURING SYSTEM, LIVER TISSUE CULTURING METHOD, AND LIVER FUNCTION EVALUATION METHOD

(71) Applicants: SHIMADZU CORPORATION, Kyoto-shi, Kyoto (JP); TOKYO INSTITUTE OF TECHNOLOGY, Tokyo (JP)

(72) Inventors: Yoichi Fujiyama, Kyoto (JP); Yoh-ichi Tagawa, Tokyo-to (JP)

(73) Assignees: SHIMADZU CORPORATION, Kyoto-shi, Kyoto (JP); TOKYO INSTITUTE OF TECHNOLOGY, Tokyo (JP)

(*) Notice: Subject to any disclaimer, the term of this patent is extended or adjusted under 35 U.S.C. 154(b) by 10 days.

(21) Appl. No.: 15/034,031

(22) PCT Filed: Nov. 8, 2013

(86) PCT No.: PCT/JP2013/080207
§ 371 (c)(1),
(2) Date: May 3, 2016

(87) PCT Pub. No.: WO2015/068253
PCT Pub. Date: May 14, 2015

(65) Prior Publication Data
US 2016/0281064 A1 Sep. 29, 2016

(51) Int. Cl.
*C12N 5/071* (2010.01)
*C12M 1/00* (2006.01)
(Continued)

(52) U.S. Cl.
CPC .......... *C12N 5/0697* (2013.01); *C12M 21/08* (2013.01); *C12M 23/12* (2013.01); *C12M 25/14* (2013.01); *C12M 29/04* (2013.01); *C12N 5/067* (2013.01); *C12N 5/0671* (2013.01); *G01N 33/5005* (2013.01); *G01N 33/573* (2013.01);
(Continued)

(58) Field of Classification Search
None
See application file for complete search history.

(56) References Cited

U.S. PATENT DOCUMENTS

2014/0289877 A1  9/2014 Taniguchi et al.

FOREIGN PATENT DOCUMENTS

| JP | 2011-244713 A | 12/2011 |
| WO | 2013/047639 A1 | 4/2013 |

OTHER PUBLICATIONS

Arnaoutova, Irina; et al; "The endothelial cell tube formation assay on basement membrane turns 20: state of the science and the art" Angiogenesis, 12, 267-274, 2009 (Year: 2009).*

(Continued)

*Primary Examiner* — David W Berke-Schlessel
(74) *Attorney, Agent, or Firm* — Sughrue Mion, PLLC

(57) ABSTRACT

A device for culturing a liver tissue has a culture chamber to which at least two flow channels, which are at least for introducing and discharging a culture medium, are connected. A gel which serves as a cell scaffold material is housed in the culture chamber. A co-culture system containing an endothelial cell-derived cell, a hepatocyte-derived cell and a mesenchymal cell is co-cultured on the gel in such a way that the co-culture system has a tubular structure.

7 Claims, 8 Drawing Sheets

(51) Int. Cl.
*C12M 1/12* (2006.01)
*G01N 33/50* (2006.01)
*C12M 3/00* (2006.01)
*C12M 1/32* (2006.01)
*G01N 33/573* (2006.01)
*G01N 33/68* (2006.01)

(52) U.S. Cl.
CPC . *G01N 33/6863* (2013.01); *C12N 2502/1352* (2013.01); *C12N 2502/14* (2013.01); *C12N 2502/28* (2013.01)

(56) References Cited

OTHER PUBLICATIONS

Hung, Paul J; et al; "Continuous Perfusion Microfluidic Cell Culture Array for High-Throughput Cell-Based Assays" Angiogenesis, 12, 267-274, 2009 (Year: 2009).*
Communication dated Mar. 7, 2017 from the Japanese Patent Office in counterpart Application No. 2015-546218.
Pan et al., "Evaluation of co-cultured CL-1 hepatocytes and hepatic stellate cells in rotatory cell culture system", J. South Med. Univ., 2013, vol. 33, No. 6, pp. 902-905.
Communication dated Sep. 19, 2017 from the State Intellectual Property Office of the P.R.C. in counterpart Application No. 201380080662.8.
International Search Report of PCT/JP2013/080207, dated Feb. 10, 2014. [PCT/ISA/210].
Communication dated Jan. 13, 2017, from the State Intellectual Property Office of People's Republic of China in counterpart Application No. 201380080662.8.

* cited by examiner

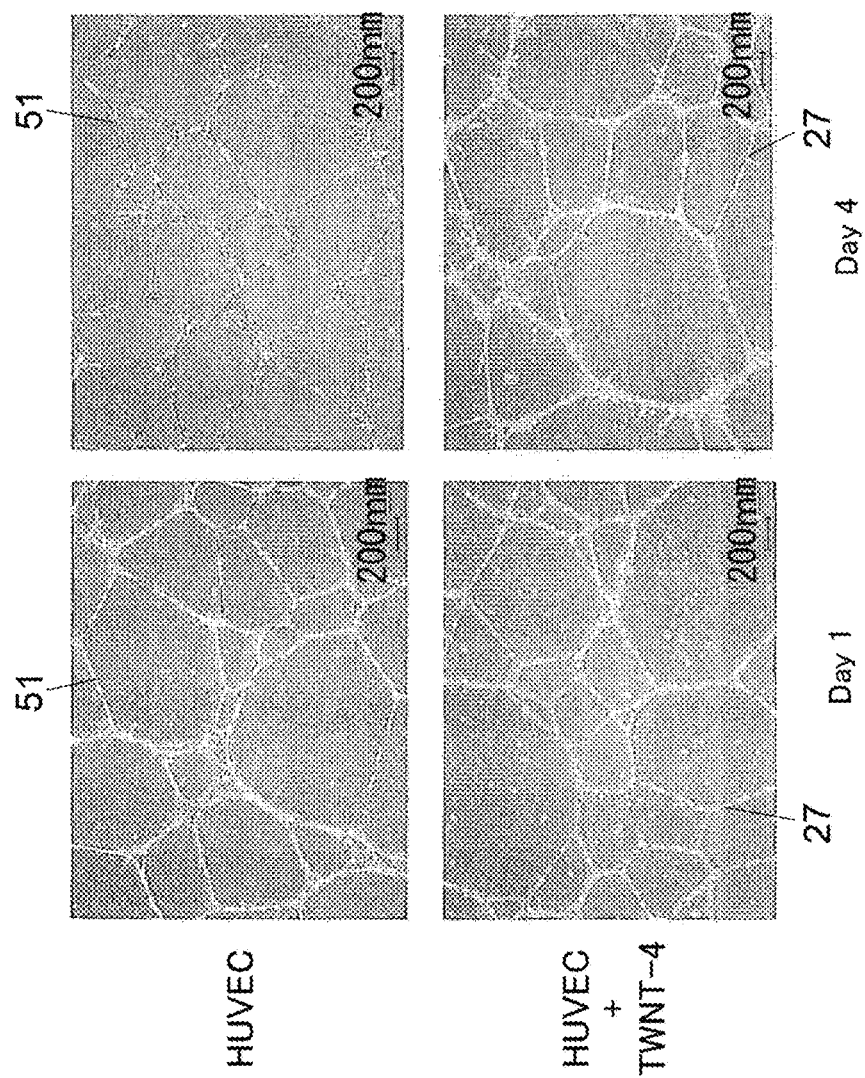

LIVER TISSUE CULTURING DEVICE, LIVER TISSUE CULTURING SYSTEM, LIVER TISSUE CULTURING METHOD, AND LIVER FUNCTION EVALUATION METHOD

CROSS REFERENCE TO RELATED APPLICATIONS

This application is a National Stage of International Application No. PCT/JP2013/080207 filed Nov. 8, 2013, the contents of all of which are incorporated herein by reference in their entirety.

TECHNICAL FIELD

The present invention relates to a device for culturing a liver tissue, a system for culturing a liver tissue, a method for culturing a liver tissue, and a method for evaluating a liver function.

BACKGROUND ART

It is effective for culturing cells to use a scaffold material suited to the cells. However, when a device is employed, there are a lot of limitations in connection with a process for manufacturing the device.

With regard to cells of organs other than the liver, in many cases, one cell has one function. On the other hand, with regard to liver cells in the liver, one liver cell has 100 or more specific functions.

However, cultured liver cells so far have not been capable of maintaining or exhibiting most of their functions. For example, many studies on a bio-artificial liver system have been conducted, but in these studies, most of drug metabolisms have not been realized.

The present inventors have reported that high liver functions are expressed by using a co-culture system of endothelial cells and hepatic parenchymal cells which forms a network structure due to the selection of a scaffold material (see Non-Patent Documents 1 and 2).

PRIOR ART DOCUMENTS

Patent Document

Patent Document 1: Japanese Patent Laid-open Publication No. 2011-244713

Non-Patent Documents

Non-Patent Document 1: Yoichi Fujiyama, Yoh-ichi Tagawa, and 5 other persons, "Analysis of liver functions in a co-culture with a hepatic parenchymal cell by using a system for culturing tubular endothelial liver cells", Proceedings of The 30th Annual Meeting of The Molecular Biology Society of Japan, 2007
Non-Patent Document 2: Yu Toyoda, Miho Tamai, Kasumi Kashikura, Shunsuke Kobayashi, Yoichi Fujiyama, Tomoyoshi Soga and Yoh-ichi Tagawa, "Acetaminophen-Induced Hepatotoxicity in a Liver Tissue Model Consisting of Primary Hepatocytes Assembling around an Endothelial Cell Network", DRUG METABOLISM AND DISPOSITION, 2012, Vol. 40, 169-177

SUMMARY OF THE INVENTION

Problems to be Solved by the Invention

The present inventors have previously reported that a network-forming co-culture system of endothelial cells and hepatic parenchymal cells expresses high liver functions (see Non-Patent Document 2). However, this structure starts to collapse about three days after its construction. Accordingly, there has been a problem of it being difficult to conduct a long-term test.

An object of the present invention is to maintain a structure of a network-forming co-culture system of an endothelial cell-derived cell and a hepatocyte-derived cell for a longer period of time.

Solutions to the Problems

A device for culturing a liver tissue according to the present invention comprises: a culture chamber to which at least two flow channels, which are at least for introducing and discharging a culture medium, are connected;
wherein a gel which serves as a cell scaffold material is housed in the culture chamber; and
wherein a co-culture system which contains an endothelial cell-derived cell, a hepatocyte-derived cell and a mesenchymal cell is co-cultured on the gel in such a way that the co-culture system has a tubular structure.

A system for culturing a liver cell according to the present invention comprises, by connecting a pump to the device for culturing the liver cell according to the present invention, a function which continuously feeds the culture medium into the culture chamber or a function which continuously sucks the culture medium from the culture chamber.

A method for culturing a liver cell according to the present invention comprises: seeding at least an endothelial cell-derived cell, a hepatocyte-derived cell, and a mesenchymal cell on a gel which serves as a cell scaffold material; and co-culturing the cells to culture a co-culture system which contains at least the endothelial cell-derived cell, the hepatocyte-derived cell, and the mesenchymal cell as well as which has a tubular structure.

A method for evaluating a liver function according to the present invention comprises evaluating a liver function by using a co-culture system which is cultured according to the method for culturing a liver cell according to the present invention.

Effects of the Invention

The device for culturing the liver tissue, the system for culturing the liver cell, the method for culturing the liver cell, and the method for evaluating the liver function according to the present invention make it possible to maintain the structure of the network-forming co-culture system of the endothelial cell-derived cell and the hepatocyte-derived cell for a longer period of time.

BRIEF DESCRIPTION OF THE DRAWINGS

FIG. 8 shows photographs showing the result of a co-culture of endothelial cells and hepatic parenchymal cells, and that of a co-culture to which stellate cells are added in addition to endothelial cells and hepatic parenchymal cells, respectively, by using the device for culturing the liver tissue shown in FIG. 1.

EMBODIMENTS OF THE INVENTION

Figure 1:
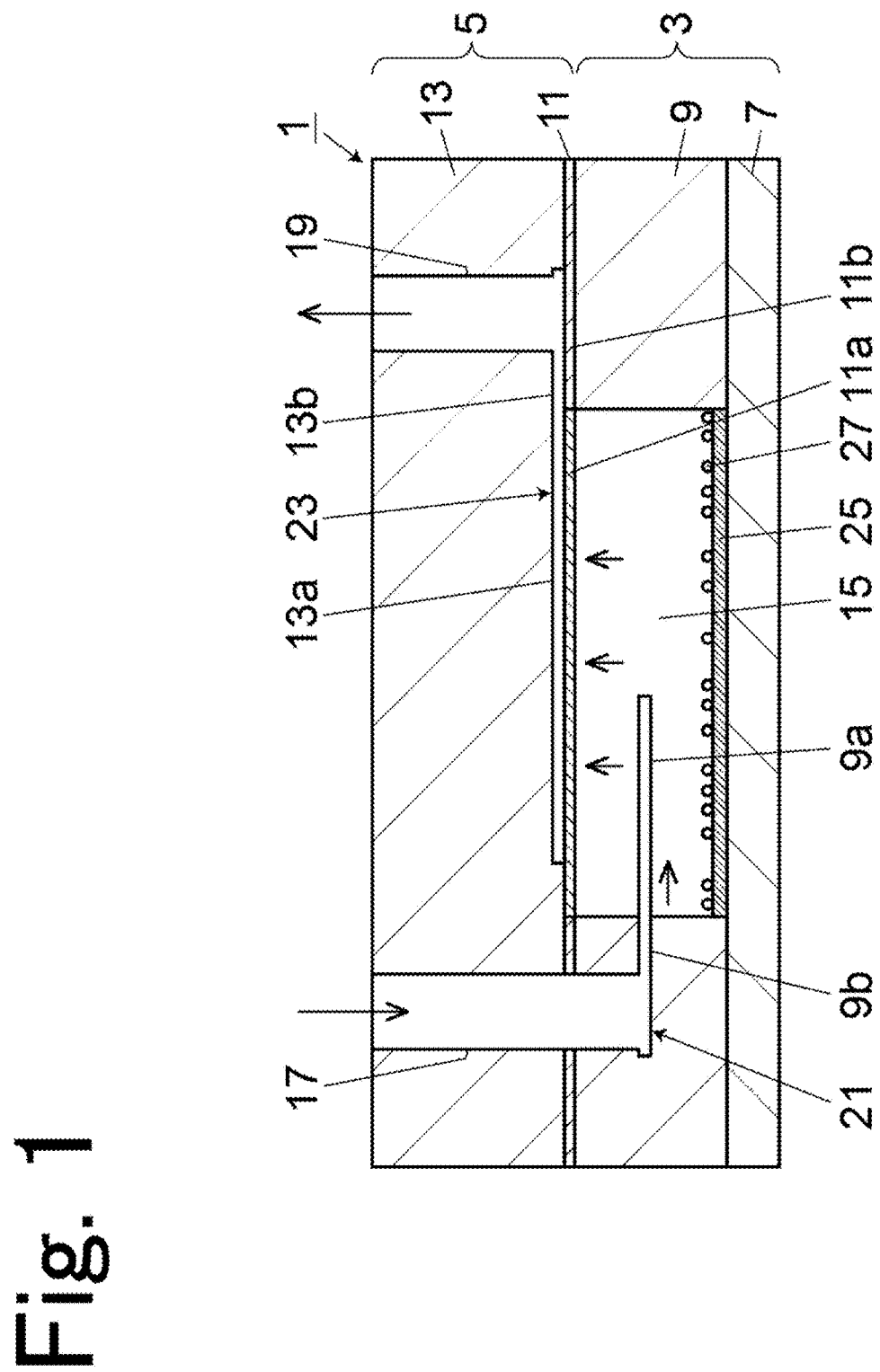
FIG. 1 shows a cross-sectional schematic diagram for illustrating one Example of a device for culturing a liver tissue.

In the device for culturing the liver tissue according to the present invention, it is preferable that the gel contains at least a laminin, a collagen, and an entactin.

In addition, in the device for culturing the liver tissue according to the present invention, it is preferable that the gel contains at least an EHS (Engelbreth-Holm-Swarm)-gel.

Further, in the device for culturing the liver tissue according to the present invention, it is preferable that the mesenchymal cell is a stellate cell-derived cell or a fibroblast.

Furthermore, in the device for culturing the liver tissue according to the present invention, an example can be given where a culture chamber part and a lid part of the culture chamber are openable and closable, and where a filter is disposed on an exit side flow channel which is one of the two flow channels. However, the structure of the device for culturing the liver tissue according to the present invention is not limited to this example.

In addition, in the device for culturing the liver tissue according to the present invention, an example can be given where a PDMS or a silicone rubber is used for at least a part of the culture chamber. However, the structure of the device for culturing the liver tissue according to the present invention is not limited to this example.

In the method for culturing the liver cell according to the present invention, it is preferable that the gel contains at least a laminin, a collagen, and an entactin.

In addition, in the method for culturing the liver cell according to the present invention, it is preferable that the gel contains at least an EHS-gel.

Further, in the method for culturing the liver cell according to the present invention, it is preferable that the mesenchymal cell is a stellate cell-derived cell or a fibroblast.

Furthermore, in the method for culturing the liver cell according to the present invention, it is preferable that a culture medium is continuously supplied to the co-culture system. However, the method for culturing the liver cell according to the present invention also includes a constitution where a culture medium is intermittently supplied to the co-culture system, instead of being continuously supplied.

In addition, in the method for culturing the liver cell according to the present invention, an example can be given where the device for culturing the liver cell according to the present invention or the system for culturing the liver cell according to the present invention is used. However, the method for culturing the liver cell according to the present invention is not limited to this example.

As an example, when endothelial cells are cultured by using a special scaffold material such as an EHS-gel, the endothelial cells form a tubular network structure. When hepatic parenchymal cells are co-cultured with the endothelial cells, the hepatic parenchymal cells migrate to the network of the endothelial cells, and have a structure similar to that of a liver tissue in vivo, and therefore, express high liver functions. However, this structure has been maintained for only about 3 days. The present inventors have found that a tubular structure similar to that of a liver tissue in vivo can be maintained for a long period of time by adding mesenchymal cells, for example, stellate cells to this tubular structure.

The use of the device for culturing the liver tissue or the system for culturing the liver tissue according to the present invention makes it possible to maintain a good culture environment by continuously supplying or intermittently supplying a culture medium from a flow channel to a culture chamber. The device for culturing the liver tissue and the system for culturing the liver tissue according to the present invention are capable of realizing an environment which is very similar to that in vivo and which cannot be realized on a petri dish. Accordingly, the device for culturing the liver tissue and the system for culturing the liver tissue according to the present invention are capable of being a device and a system which can maintain a tubular structure having high liver functions for a long period of time.

The method for culturing the liver tissue according to the present invention is capable of maintaining a network-forming tubular structure of a co-culture system which contains endothelial cell-derived cells, hepatocyte-derived cells, and mesenchymal cells for a longer period of time. In particular, the method for culturing the liver tissue according to the present invention which uses the device for culturing the liver tissue or the system for culturing the liver tissue according to the present invention is capable of culturing a co-culture system which contains endothelial cell-derived cells, hepatocyte-derived cells, and mesenchymal cells in an environment which is very similar to that in vivo.

The method for evaluating the liver function according to the present invention is capable of evaluating a liver function by using a co-culture system which contains endothelial cell-derived cells, hepatocyte-derived cells, and mesenchymal cells, the co-culture system being cultured according to the method for culturing the liver tissue according to the present invention. In particular, the method for evaluating the liver function according to the present invention which uses a co-culture system which is cultured according to the method for culturing the liver cell according to the present invention which uses the device for culturing the liver tissue or the system for culturing the liver tissue according to the present invention is capable of evaluating a liver function in an environment which is very similar to that in vivo.

The present invention is a technique for culturing cells, in particular, a useful technique which is used for an artificial organ such as an artificial liver or a drug metabolism test.

Figure 2:
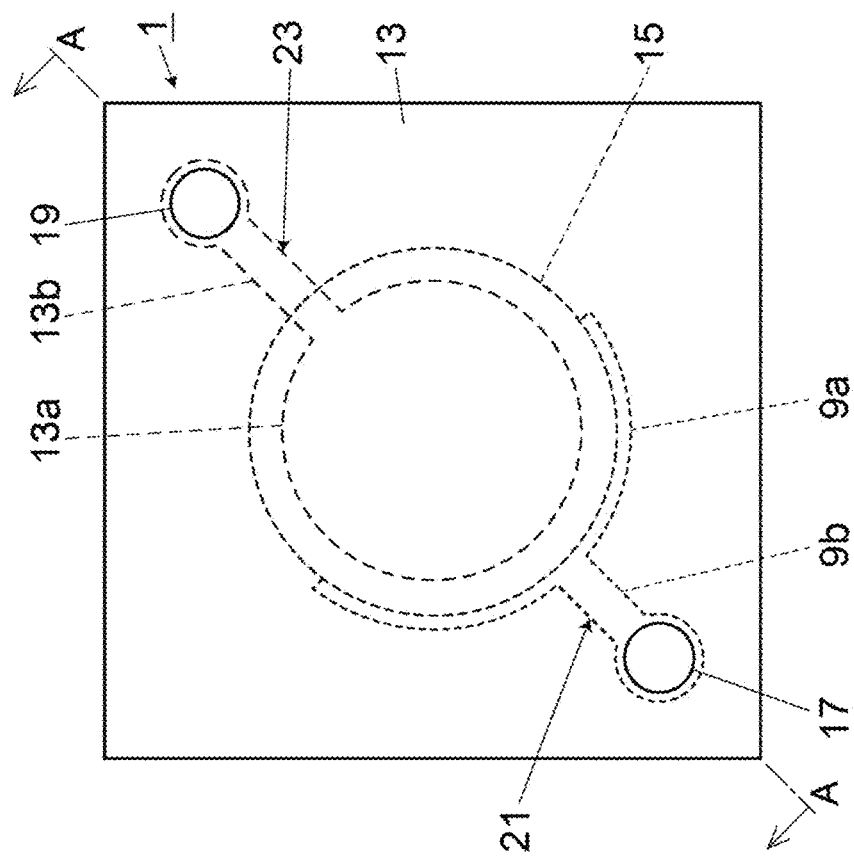
FIG. 2 shows a plan view of the same Example.

FIG. 1 shows a cross-sectional schematic diagram for illustrating one Example of a device for culturing a liver tissue. FIG. 2 shows a plan view of the same Example. The section shown in FIG. 1 corresponds to position A-A shown in FIG. 2.

A device for culturing a liver tissue 1 is roughly formed by a culture chamber part 3 and a lid part 5. The culture chamber part 3 has a base plate 7 and a PDMS structure body 9. The lid part 5 has a filter supporting layer 11 and a PDMS structure body 13.

The base plate 7 is, for example, formed of synthetic quartz. The PDMS structure body 9 and the PDMS structure body 13 are, for example, formed of SILPOT 184 (manufactured by Dow Corning Toray Co., Ltd.). The filter supporting layer 11 has, for example, a structure in which a filter 11a made of a porous membrane is sandwiched between silicone rubber sheets 11b. The filter 11a is, for example, a commercially available filter made of polycarbonate (manufactured by Whatman, CYCLOPORE 7062-2513).

Each of these members has a plane shape with a width of 20 mm (millimeters) and a length of 20 mm. The thickness of the base plate 7 is, for example, 1 mm. The thickness of the PDMS structure body 9 is, for example, 3 mm. The thickness of the porous membrane which constitutes the filter 11a is, for example, 0.25 mm. The thickness of the silicone rubber sheet 11b is, for example, 0.2 mm. The thickness of the PDMS structure body 13 is, for example, 3 mm.

A culture chamber 15, which is constituted by a through hole, is formed in the center of the PDMS structure body 9. The diameter of the culture chamber 15 is, for example, 10 mm. A groove 9a which is provided on the side wall of the culture chamber 15, and a groove 9b which is connected to the groove 9a are formed in the PDMS structure body 9. The depth of each of the groove 9a and the groove 9b is, for example, 0.1 mm. The width of the groove 9b is, for example, 1 mm. The length of the groove 9b is, for example, about 5 mm.

The PDMS structure body 9 has, for example, a two-layer structure. The grooves 9a and 9b are formed by a recessed part, which is formed by templating on the surface of one layer of PDMS out of two layers of PDMS which constitute the PDMS structure body 9. The grooves 9a and 9b are disposed on the laminating surface of the two layers of PDMS.

The filter 11a is disposed in the center of the filter supporting layer 11. The diameter of the filter 11a is, for example, 11 mm. The filter 11a is disposed in a position which covers the upper part of the culture chamber 15. A through hole is formed in the center of the silicone rubber sheet 11b. The filter 11a is disposed in the through hole. The silicone rubber sheet 11b holds the filter 11a in such a way that the filter 11a tightly adheres to the PDMS structure body 13.

A circular recessed part 13a is formed in the center of the PDMS structure body 13. The diameter of the recessed part 13a is, for example, 8 mm. The depth of the recessed part 13a is, for example, 0.1 mm. A groove 13b which is connected to the recessed part 13a is also formed in the PDMS structure body 13. The groove 13b is formed by performing templating of PDMS. The depth of the groove 13b is, for example, 0.1 mm. The width of the groove 13b is, for example, 1 mm. The length of the groove 13b is, for example, about 5 mm.

The PDMS structure body 9, the silicone rubber sheet of the filter supporting layer 11 and the PDMS structure body 13 are provided with a through hole 17 which is connected to the groove 9b. The PDMS structure body 13 is provided with a through hole 19 which is connected to the groove 13b. The diameter of each of the through hole 17 and the through hole 19 is, for example, 1.5 mm. The through hole 17 and the through hole 19 are, for example, formed by through-hole processing.

The groove 9a, the groove 9b and the through hole 17 form an inlet side flow channel 21 of a culture medium. The recessed part 13a, the groove 13b and the through hole 19 form an exit side flow channel 23 of the culture medium.

The base plate 7 and the PDMS structure body 9 are stuck to form the culture chamber part 3. In addition, the filter supporting layer 11 and the PDMS structure body 13 are stuck to form the lid part 5. When each of members is stuck, it is preferable that joining is performed after a joining surface of each of members is activated by oxygen plasma or ultraviolet rays in order to achieve strong adhesion.

The device for culturing the liver tissue 1 according to the Present Example is formed by superimposing the lid part 5 on the upper side of the culture chamber part 3. A silicone rubber which constitutes a part of the filter supporting layer 11 has a self-adsorption property, and therefore, the lid part 5 is easily detachable from the culture chamber part 3.

Such a structure of the device for culturing the liver tissue 1 is, for example, disclosed in Patent Document 1.

A gel 25 serving as a cell scaffold material is housed in the culture chamber 15 of the device for culturing the liver tissue 1. The gel 25 is, for example, an EHS-gel. An EHS-gel is a preparation of basement membranes isolated from EHS mouse sarcoma cells, and is rich in laminins, collagen type IV, and proteoglycans. The EHS-gel liquefies at a low temperature, and solidifies at normal temperature. Accordingly, the EHS-gel can be solidified on the bottom surface of the culture chamber 15 by pouring the EHS-gel into the culture chamber 15 in a state where the device for culturing the liver tissue 1 is cooled, and then allowing the EHS-gel to stand, for example, in an incubator at 37° C. or at room temperature. Meanwhile, such coating with a scaffold material may be conducted in the production process of the device for culturing the liver tissue 1, or may be conducted by a user who has purchased the device for culturing the liver tissue 1.

In the culture chamber 15, a co-culture system 27 which contains endothelial cell-derived cells, hepatocyte-derived cells, and mesenchymal cells is co-cultured on the gel 25 so that the co-culture system 27 has a tubular structure. Examples of the endothelial cell-derived cells include sinusoidal endothelial cells, human umbilical vein (artery) endothelial cells, TD2, GH7, and the like. Examples of the hepatocyte-derived cells include hepatic parenchymal cells, HepaRG, Huh-7, Hep G2, TLR2, Hepa 1-6, liver progenitor cells, and the like. Examples of the mesenchymal cells include stellate cell-derived cells, fibroblasts, HFO, NIH-3T3, mouse embryonic fibroblasts, and the like. Examples of the stellate cell-derived cells include stellate cells, TWNT-4, LX-2, LI90, RI-T, and the like.

Figure 3:
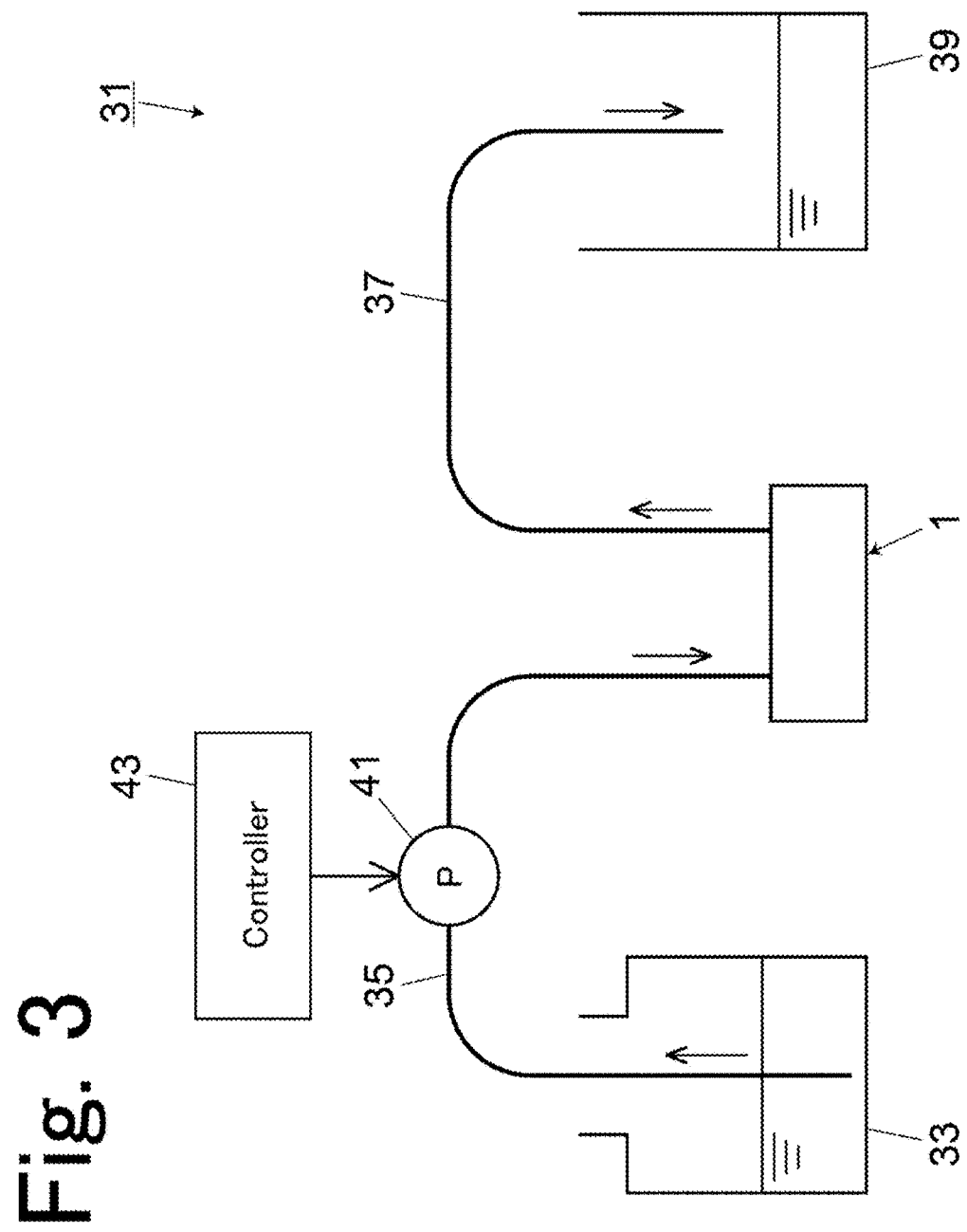
FIG. 3 shows a schematic diagram for illustrating one Example of a system for culturing a liver cell.

FIG. 3 shows a schematic diagram for illustrating one Example of a system for culturing a liver cell which uses the device for culturing the liver tissue 1 according to the Present Example.

A system for culturing a liver cell 31 is a combination of the device for culturing the liver tissue 1 and a liquid feeding mechanism which continuously feeds a culture medium into the device for culturing the liver tissue 1. The liquid feeding mechanism has a culture medium housing part 33, a culture medium supply pipe 35, a culture medium discharge pipe 37, a waste liquid housing part 39, a liquid feeding pump 41, and a controller 43.

One end of the culture medium supply pipe 35 is inserted into the culture medium housing part 33. The other end of the culture medium supply pipe 35 is connected to the inlet side flow channel 21 of the device for culturing the liver tissue 1. One end of the culture medium discharge pipe 37 is connected to the exit side flow channel 23 of the device for culturing the liver tissue 1. The other end of the culture medium discharge pipe 37 is inserted into the waste liquid housing part 39. The liquid feeding pump 41 is connected to the culture medium supply pipe 35. The controller 43 controls the operation of the liquid feeding pump 41.

The culture medium housed in the culture medium housing part 33 is suctioned by the liquid feeding pump 41, and is sent to the device for culturing the liver tissue 1 through the culture medium supply pipe 35. The culture medium supplied to the device for culturing the liver tissue 1 is introduced into the culture chamber 15 from the peripheral surface of the culture chamber 15 by passing through the inlet side flow channel 21, as shown by arrows in FIG. 1.

In accordance with the introduction of the culture medium into the culture chamber 15, apart of the culture medium within the culture chamber 15 is discharged from the culture chamber 15 to the outside through a filter part of the filter supporting layer 11 and the exit side flow channel 23, as shown by arrows in FIG. 1. The culture medium discharged to the outside of the device for culturing the liver tissue 1 is discharged to the waste liquid housing part 39 through the culture medium discharge pipe 37.

When the culture medium within the culture chamber 15 is discharged from the exit side flow channel 23, the device for culturing the liver tissue 1 allows the culture medium to pass through the filter part of the filter supporting layer 11, and therefore, it is possible to reduce probability of clogging of the exit side flow channel 23 with the gel 25 peeled off.

In addition, as shown in FIG. 2, in the device for culturing the liver tissue 1, the recessed part 13a, which constitutes an end part of the flow channel of the exit side flow channel 23, has a larger area than an end part of the groove 13b, and therefore, a locally strong liquid flow is hardly generated. Accordingly, the device for culturing the liver tissue 1 also achieves an effect of suppressing peeling-off of the gel 25.

As described above, the device for culturing the liver tissue 1 is advantageous for culturing cells for a long period of time.

In the system for culturing the liver cell 31 shown in FIG. 3, the culture medium supply pipe 35 is provided with the liquid feeding pump 41 and has a function to continuously feed the culture medium into the culture chamber 15, but the system for culturing the liver cell according to the present invention is not limited thereto.

Figure 4:
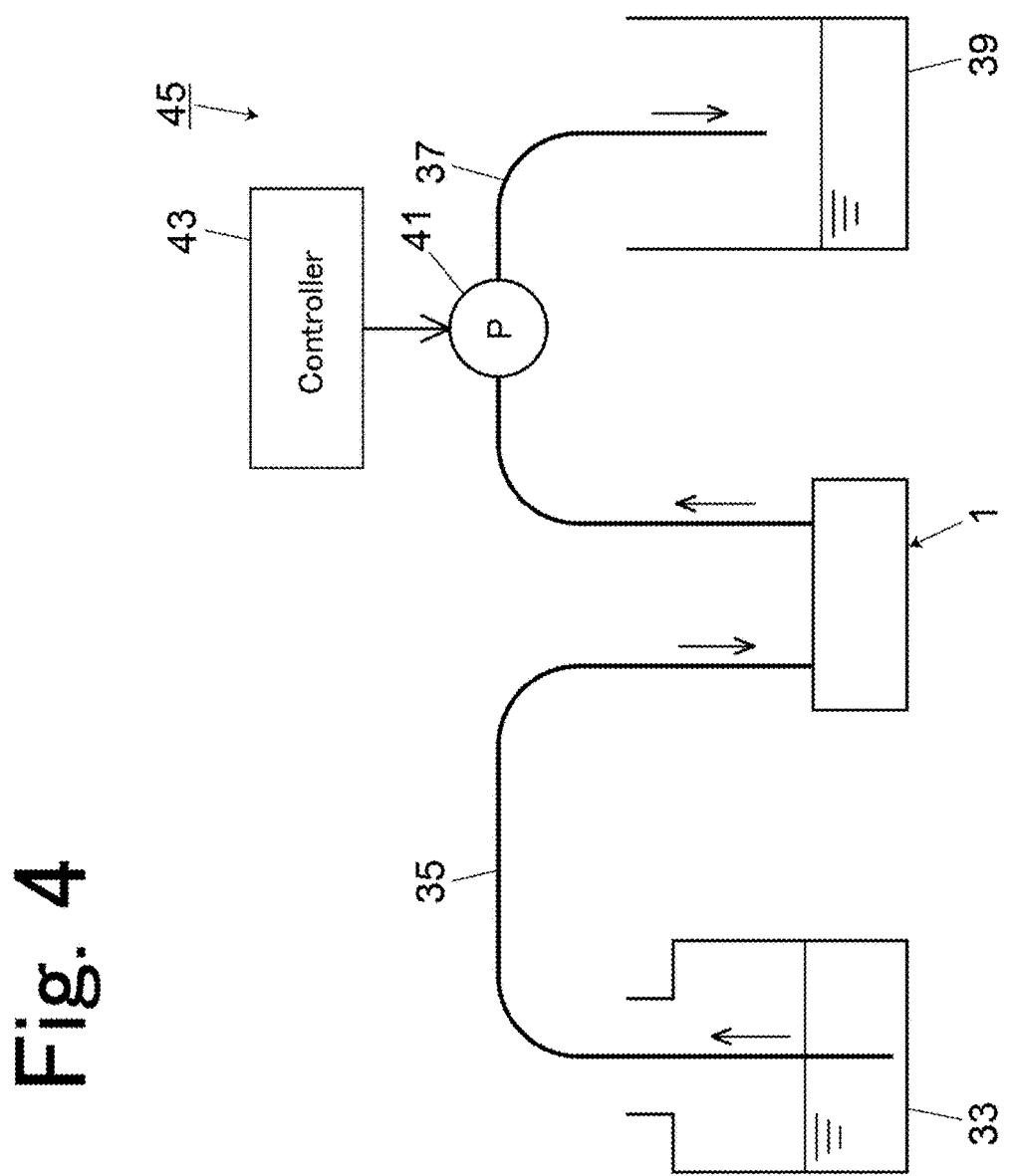
FIG. 4 shows a schematic diagram for illustrating another Example of a system for culturing a liver cell.

As an example, as shown in FIG. 4, a system for culturing a liver cell 45, which is an Example of the present invention, may be a system in which the culture medium discharge pipe 37 is provided with the liquid feeding pump 41 and has a function to continuously suck the culture medium from the inside of the culture chamber 15. Meanwhile, the system for culturing the liver cell according to the present invention is not limited to the constitution shown in FIG. 3 or FIG. 4.

Next, an example of the step of culturing the co-culture system 27 containing endothelial cell-derived cells, hepatocyte-derived cells, and mesenchymal cells by using the device for culturing the liver tissue 1 will be described.

First, the culture chamber part 3 and the lid part 5 are subjected to sterilization treatment by using an autoclave, an alcohol, and the like. The sterilized culture chamber part 3 and the sterilized lid part 5 are stuck to each other. An EHS-gel which has been cooled is poured into the culture chamber 15 to supply the EHS-gel to the whole bottom surface of the culture chamber 15. The EHS-gel is gelled, for example, at 37° C. to fix the gel 25 made of the EHS-gel within the culture chamber 15.

Sinusoidal endothelial cells are seeded on the gel 25 to form an endothelial cell network. Stellate cells are seeded on the endothelial cells constructing a network structure, and hepatic parenchymal cells are also seeded thereon. As a result, stellate cells are incorporated into the endothelial cell network, and liver cells migrate into the area surrounding the cell network, and then the co-culture system 27 which has a structure similar to that of an actual liver is formed.

Meanwhile, the order of seeding the endothelial cell-derived cells, the hepatocyte-derived cells, and the mesenchymal cells is not limited to the above-described order. For example, the endothelial cell-derived cells, the hepatocyte-derived cells and the mesenchymal cells may be seeded simultaneously. The seeding may be in the order of the endothelial cell-derived cells, the hepatocyte-derived cells, and the mesenchymal cells.

Then, a cell culture experiment conducted by using the device for culturing the liver tissue 1 will be described.

Figure 5:
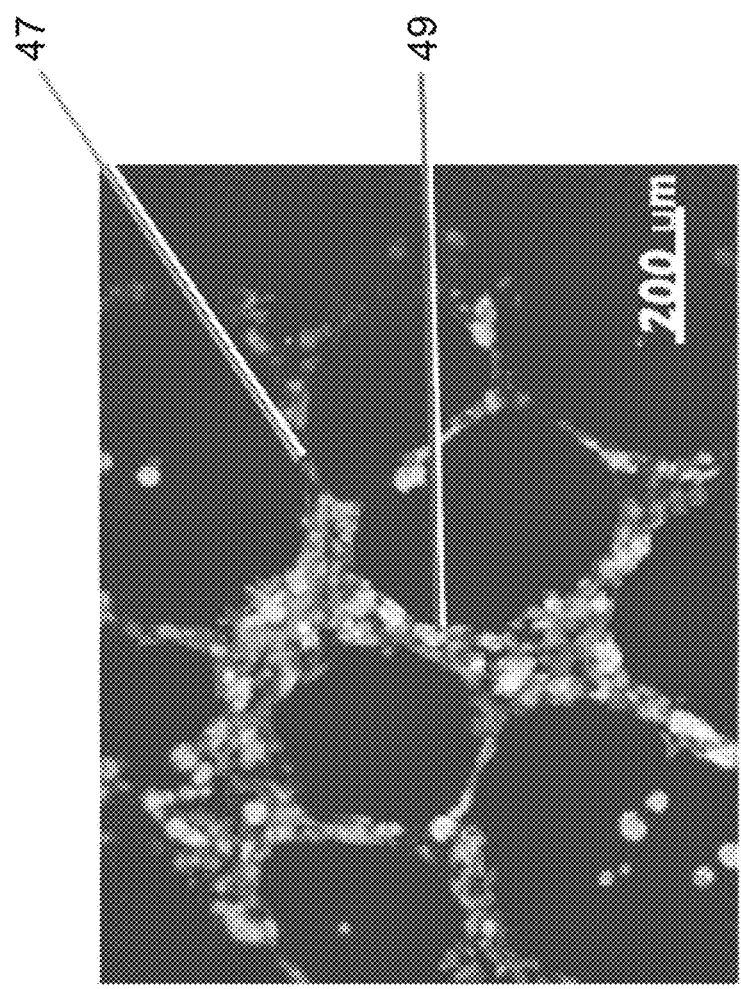
FIG. 5 shows a photograph showing a state of network-forming sinusoidal endothelial cells and hepatic parenchymal cells on an EHS-gel.
Figure 6:
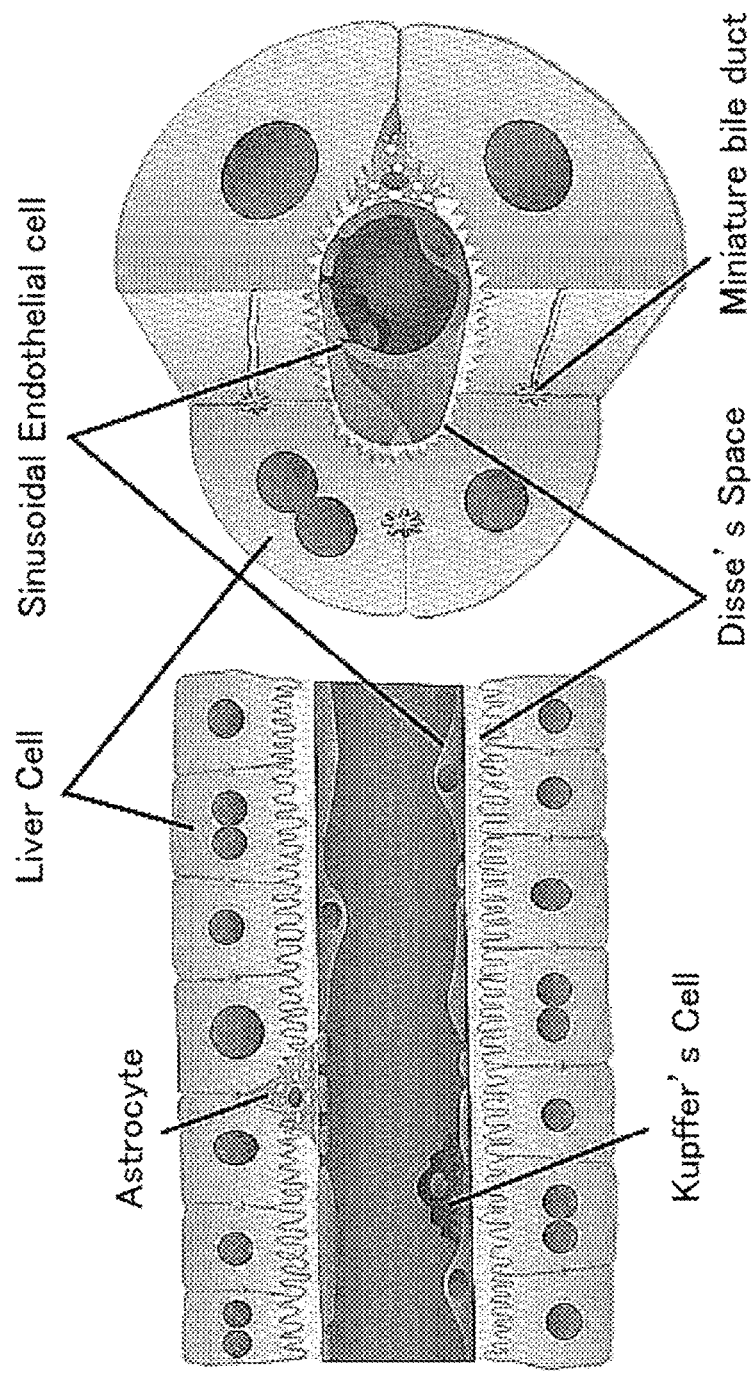
FIG. 6 shows a schematic perspective view and a schematic cross section showing a structure of a network-forming co-culture system containing endothelial cell-derived cells, hepatocyte-derived cells, and mesenchymal cells partly in section.

FIG. 5 shows a photograph showing a state of network-forming sinusoidal endothelial cells and hepatic parenchymal cells on an EHS-gel which is achieved by using the device for culturing the liver tissue 1 according to the Present Example. Meanwhile, no mesenchymal cell is co-cultured in FIG. 5. FIG. 6 shows a schematic perspective view and a schematic cross section showing a structure of a network-forming co-culture system containing endothelial cell-derived cells, hepatocyte-derived cells and mesenchymal cells partly in section.

Sinusoidal endothelial cells were seeded into the culture chamber 15 which had been coated with an EHS-gel to form an endothelial cell network, and thereafter, hepatic parenchymal cells were seeded on the endothelial cells, and then the cells were cultured. As apparent from the photograph shown in FIG. 5, hepatic parenchymal cells 49 migrate into a network of endothelial cells 47, and it is found that the cells have a structure similar to that of an in vivo liver tissue.

Figure 7:
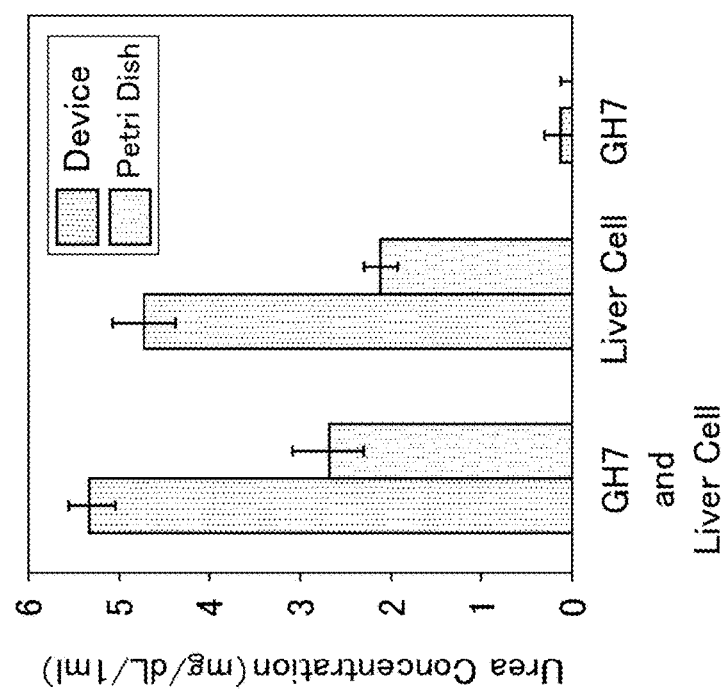
FIG. 7 shows a diagram showing the results of an evaluation test for a liver function conducted by using liver cells.

The results of an evaluation test for a liver function conducted by using the above-described liver cells are shown in FIG. 7. The device for culturing the liver tissue 1 according to the Present Example ("Device" in the figure) and a typical petri dish for cell culture ("Petri dish" in the figure) as a Comparative Example were used. Each of the above-described sinusoidal endothelial cells ("GH7" in the figure) and the hepatic parenchymal cells ("Liver cell" in the figure) was cultured alone or they were cultured together as a co-culture system of both types of cells, and then the urea synthetic ability of each of the cultured cells was evaluated. The urea synthetic ability is a liver function which decomposes ammonia and synthesizes urea. In the culture conducted by using the device for culturing the liver tissue, the supply of the culture medium was conducted by feeding the medium continuously for 24 hours at a flow rate of 40 μL/h (microliters/hour). In the culture conducted by using the petri dish, the culture medium was exchanged at every fixed interval of time.

As apparent from FIG. 7, as compared to the case where the hepatic parenchymal cells were cultured alone, the co-culture system showed a higher liver function. In particular, as compared to the case where the cells were cultured in the petri dish, the cells which were cultured by using the device for culturing the liver tissue according to the present invention showed a higher liver function. The reason is considered that, in the culture conducted by using the device for culturing the liver tissue, the tissue received a shear stress (shearing stress) because the culture medium was continuously supplied to the cells, and therefore, the cells were cultured under an environment more similar to an in vivo environment.

In addition, the device for culturing the liver tissue 1 according to the Present Example can prevent clogging of a flow channel due to peeling-off of a scaffold material as described above. Accordingly, the device for culturing the liver tissue 1 can culture liver cells under an environment similar to the in vivo environment for a long period of time stably. For this reason, the device for culturing the liver tissue 1 can be used for studies on various systems such as a drug metabolism test, and also, it can be expected that the device for culturing the liver tissue 1 is used for development of an artificial liver.

However, there has been a problem in a co-culture system of sinusoidal endothelial cells and hepatic parenchymal cells that the structure tends to collapse after only about 3 days. The present inventors have found that a network structure can be maintained for a long period of time by adding stellate cells to the co-culture system of sinusoidal endothelial cells and hepatic parenchymal cells.

FIG. 8 shows photographs showing the result of a co-culture of endothelial cells and hepatic parenchymal cells and that of a co-culture to which stellate cells are added in addition to endothelial cells and hepatic parenchymal cells, by using the device for culturing the liver tissue 1 according to the Present Example.

Preparation of the gel 25, seeding of each of the cells, and supply of the culture medium were conducted in the same manner as the Example described above.

Conditions of seeding cells are as follows:
GH7: $5 \times 10^5$ cells/$\phi$ 3.5 cm (10% FBS-DMEM (a product of Invitrogen))
Hepatocyte: $5 \times 10^5$ cells/$\phi$ 3.5 cm (10% FBS-DMEM (a product of Invitrogen))
HUVEC: $4 \times 10^5$ cells/$\phi$ 3.5 cm (EGM-2: Endothelial Cell Growth Medium Kit-2 (a product of Lonza))
TWNT-4: $1 \times 10^5$ cells/$\phi$ 3.5 cm (10% FBS-DMEM (a product of Invitrogen))

As understood from the results shown in FIG. 8, as compared to a co-culture system 51 of endothelial cells and hepatic parenchymal cells, the co-culture system 27 containing endothelial cell-derived cells, hepatocyte-derived cells and mesenchymal cells can realize the maintenance of a network structure for a long period of time by adding stellate cells (TWNT-4).

A liver function can be studied by using the device for culturing the liver tissue according to the present invention or the system for culturing the liver tissue according to the present invention. Specifically, it can be considered that the device for culturing the liver tissue according to the present invention or the system for culturing the liver tissue according to the present invention can be used for an analytical system, which is capable of searching a biologically active substance, for example, a pharmacokinetic test and the like.

Meanwhile, stellate cells (TWNT-4) were added as the mesenchymal cells, but when stellate cells other than TWNT-4 are added, the long-term maintenance of a network structure can also be realized. In addition, when the mesenchymal cells other than stellate cells are added, the long-term maintenance of a network structure can also be realized.

The Example of the present invention is described hereinabove, but the constitution, disposition, numerical values, and the like in the Example are only given as examples, and the present invention is not limited thereto. Various modifications are possible within the scope of the present invention which is described in claims.

As an example, in the above-described Example, an EHS-gel is used as a gel which serves as a cell scaffold material, but a gel which can be used in the present invention is not limited thereto. The gel which can be used in the present invention should be any gel on which a co-culture system containing an endothelial-derived cell, a hepatocyte-derived cell, and a mesenchymal cell forms a tubular structure, preferably a network structure. The gel which can be used in the present invention is not limited to an EHS-gel, but the gel may be, for example, a gel containing at least a laminin, a collagen and an entactin, or may be a gel in which other ingredients are added to an EHS-gel.

DESCRIPTION OF REFERENCE SIGNS

1: Device for culturing liver tissue
3: Culture chamber part
5: Lid part
15: Culture chamber
21: Inlet side flow channel
23: Exit side flow channel
25: Gel
27: Co-culture system containing endothelial cell-derived cells, hepatocyte-derived cells and mesenchymal cells
31, 45: System for culturing liver tissue

The invention claimed is:

1. A method for culturing a liver tissue comprising: seeding at least an endothelial cell, a hepatocyte, and a mesenchymal cell on a gel which serves as a cell scaffold material; and co-culturing the cells to culture a co-culture system which contains at least the endothelial cell, the hepatocyte, and the mesenchymal cell,
   wherein the mesenchymal cell is a stellate cell or a fibroblast,
   and wherein the system has a tubular structure.

2. The method for culturing the liver tissue according to claim 1, wherein the gel contains at least a laminin, a collagen, and an entactin.

3. The method for culturing the liver tissue according to claim 1, wherein the gel contains at least an EHS-gel.

4. The method for culturing the liver tissue according to claim 1, the method comprising continuously supplying a culture medium to the co-culture system.

5. The method for culturing the liver tissue according to claim 1, wherein a device for culturing the liver cell is used;
   the device for culturing a liver tissue comprising: a culture chamber to which at least to flow channels, which are at least for introducing and discharging a culturing medium, are connected; wherein a gel serves as a cell scaffold material is housed in the culture chamber; and wherein a co-culture system which contains an endothelial cell, a hepatocyte, and a mesenchymal cell is co-cultured on the gel in such a way that the co-culture system has a tubular structure,
   wherein the mesenchymal cell is a stellate cell or a fibroblast.

6. A method for evaluating a liver function comprising evaluating a liver function by using the co-culture system which is cultured according to the method for culturing the liver tissue according to claim 1.

7. The method of claim 1, wherein the cells are co-cultured for three days or more.

* * * * *